United States Patent [19]

Hilleman et al.

[11] Patent Number: 4,459,286
[45] Date of Patent: Jul. 10, 1984

[54] **COUPLED *H. INFLUENZAE* TYPE B VACCINE**

[75] Inventors: Maurice R. Hilleman, Lafayette Hill; Joseph Y. Tai, Fort Washington, both of Pa.; Richard L. Tolman, Warren, N.J.; Philip P. Vella, North Wales, Pa.

[73] Assignee: Merck & Co., Inc., Rahway, N.J.

[21] Appl. No.: 462,594

[22] Filed: Jan. 31, 1983

[51] Int. Cl.$^3$ .................. A61K 39/40; A61K 39/095; A61K 39/102; C07G 7/00

[52] U.S. Cl. ........................................ 424/87; 424/85; 424/88; 424/92; 260/112 R

[58] Field of Search .................. 424/88, 92, 85, 87; 260/112 R

[56] References Cited

U.S. PATENT DOCUMENTS 4,220,717 9/1980 Kuo ........................................ 424/92
4,271,147 6/1981 Helting et al. ........................ 424/92

OTHER PUBLICATIONS

Schneerson et al., New Dev. with Hum. & Vet. Vaccines, pp. 77-97, 1980.
Anderson et al., Inf. & Imm., vol. 15, pp. 472-477, 1980.
Helting et al., Actapath. Microbiol. Scand. Sect. C., vol. 89, pp. 69-78, 1982.
Schneerson et al., J. Exp. Med., vol. 152, pp. 361-376, 1980.
Rosenberg et al., J. Biol. Chemistry, vol. 236, pp. 2845-2849, 1961.

*Primary Examiner*—Blondel Hazel
*Attorney, Agent, or Firm*—Gabriel Lopez; Richard A. Elder; Hesna J. Pfeiffer

[57] ABSTRACT

*Haemophilus influenzae* type B polysaccharide is coupled through a spacer to a serotype outer membrane protein from *Neisseria meningitidis*. This conjugate has enhanced antigenicity and immunogenicity relative to the unconjugated polysaccharide.

7 Claims, No Drawings

COUPLED *H. INFLUENZAE* TYPE B VACCINE

BACKGROUND OF THE INVENTION

*Haemophilus influenzae* type b (Hib) is the most important cause of endemic bacterial meningitis in infants and has also been identified as the leading cause of acquired mental retardation in the United States. Various investigations clearly indicated that the type-specific capsular polysaccharide of *H. influenzae* type b is the principal virulent factor in invasive infections by this organism. There is much evidence that serum antibodies to the polysaccharide confer immunity to diseases caused by *H. influenzae* type b. Vaccination with the purified capsular polysaccharide in adults and children older than two years has been shown to be effective. However, the polysaccharide failed to elicit sufficient serum antibody to provide protection in young infants less than 15 months of age, who are the most susceptible to the infection. It is, therefore, necessary to create a new and efficacious vaccine aimed at this age group. This is particularly important because, although the mortality for Hib-related disease has been reduced to about 5-10% by antibiotic treatment, the morbidity rate remains at 30-50%. (Schneerson et al., *Haemophilus Influenzae* Type B Polysaccharide-Protein Conjugates: Model for a New Generation of Capsular Polysaccharide Vaccines, New Dev. with Hum. & Vet. Vaccines, 77-94, 1980).

SUMMARY OF THE INVENTION

*H. influenzae* type b polysaccharide is coupled to the serotype protein (major outer membrane protein) of *Neisseria meningitidis* through a spacer, 6-aminocaproic acid. In the animal model, the conjugate is highly immunogenic, producing antibody to the polysaccharide at least 30 fold over the polysaccharide alone. In addition, the conjugate gives essentially 100% immunoglobulin G which is the most desirable class for long lasting protections.

DETAILED DESCRIPTION

*H. influenzae* type B polysaccharide used in this invention has been described by Rosenberg and Zamenhof, J. Biol. Chem. 236, 2845-2849 (1961), and Zamenhof et al., J. Biol. Chem. 203, 695-704 (1953). The proposed structure is based on equimolar amounts of ribose, ribitol, and phosphate: $\beta$-D-ribose-(1-1)-ribitol-5-(PO$_4$); Anderson et al., Inf. & Imm., 15, No. 2, 472-477 (1977). Hib having a $K_D$ of approximately 0.34 on a Sepharose 4B column is preferred.

The protein of this invention is the serotype outer membrane protein from *N. meningitidis* which is a T-cell stimulator. An example is the serotype 2 outer membrane protein which has been described in Helting et al., Serotype Determinant Proteins of *Neisseria Meningitidis*, Actapath. microbiol. scand. Sect. C, 89, 69-78, 1982, and Frasch et al., J. Bact., 127, 973-981 (1976).

In the process of this invention, the 6-aminocaproic acid is first covalently linked to the Hib PS to form a PS-spacer complex. This is preferred to first forming a protein-spacer complex. The PS is activated with cyanogen bromide (CNBr) at an elevated pH at about 4° C. for a short time. The activated PS is then mixed with the acid for about 24 hours, after which it is purified, as by dialysis. This PS-spacer complex is mixed in a mildly acid protein solution to which is added 1-ethyl-3-(3-dimethylaminopropyl)-carbodiimide hydrochloride. The mixture is reacted for about 2 hours at pH 4.75 after which the PS-spacer-protein conjugate is isolated, as by centrifugation and column chromatography. As described herein, the invention is said to be a protein/polysaccharide conjugate coupled through a spacer. It is not intended to limit this invention to any particular type of bonding between polysaccharide, spacer, and protein.

The conjugate of this invention may be used in mammalian species for either active or passive protection prophylactically or therapeutically against bacteremia caused by the *H. influenzae* type B organism. Passive protection can be accomplished by injecting either whole antiserum obtained from animals previously dosed with the conjugate or globulin containing the immunogenic agent, with or without a pharmaceutically acceptable carrier. Such globulin is obtained by standard techniques from whole antiserum such as electrophoresis.

In a preferred embodiment of this invention, the conjugate is used for active vaccination of humans, especially neonates.

The conjugate of this invention is used in injectable form for either active or passive immunization. By the injectable form of the conjugate of this invention is meant an effective amount of said conjugate, antisera derived from said conjugate or gammaglobulin or other antibody-containing fractions of said antisera, said injectable form further optionally comprising a pharmaceutically acceptable carrier, such as aseptic saline water. The use of an adjuvant is also intended to be within the scope of this invention.

By an effective amount is meant a quantity able to produce measurable amounts of antibodies. In man this can range from 2-50 $\mu$g per dose; preferably 10 $\mu$g/dose.

The invention is further defined by reference to the following examples, which are intended to be illustrative and not limiting.

EXAMPLE 1

Preparation of *H. Influenzae* Type B Capsular Polysaccharide

INOCULUM AND SEED DEVELOPMENT

A Stage: A lyophilized tube of *Haemophilus influenzae* type b, (cultured from Ross 768, received from State University of New York) was suspended in 1 ml of 0.85% (w/v) sterile sodium chloride and 0.2 ml was spread on Heart Infusion Broth Agar Plate. After 24 hours incubation at 37° C. in a candle jar, the growth on the plate was resuspended in 5 ml Heart Infusion Broth (HIB) (Heart Infusion Broth (Difco) 25 g/L; Yeast Extract (Difco) 3 g/L; and Dextrose 5 g/L sterilized 25 minutes at 121° C.) and 0.2 ml was spread on HIB agar (same as HIB plus Agar (Difco) 20 g/L). Four HIB agar bottles were prepared.

B Stage: 2-Liter Flask—The growth on four HIB agar plates was resuspended in 20 ml HIB and transferred into 1 liter of inoculum medium: The flask was incubated at 37° C. on a rotary shaker at 200 rpm for 7 hours.

| Inoculum Medium* | |
|---|---|
| Heart Infusion Broth (Difco) | 25 gm |
| NaCl | 5 gm |
| Yeast Extract Dialysate (Difco) | 3 gm |

-continued
Inoculum Medium*

| | |
|---|---|
| (pore size 12000 mol. wt). | |
| $K_2HPO_4$ | 2.5 gm |
| UCON LB 625 (8% solution) | 2 ml |
| (presterilized 1 hr. at 121° C.) | |
| Distilled $H_2O$ | 1 L |
| Dextrose | 5 gm |
| (sol'n of 5 gm dextrose plus 100 ml distilled $H_2O$ sterilized at 121° C. for 20 min. added aseptically prior to inoculation) | |
| NAD** | 10 mg |
| Hemin*** | 10 mg |

*Sterilized for 25 min. at 121° C. in a 2-liter non-baffled Erlenmeyer flask.
**A stock solution of NAD containing 2 mg/ml was sterilized by filtration through a Millipore filter (0.22μ) and added aseptically just prior to inoculation.
***A stock solution of Hemin 3X was prepared by dissolving 200 mg in 10 ml of 0.1M NaOH and the volume adjusted to 100 ml. The solution was sterilized for 20 minutes at 121° C. and added aseptically to the final medium prior to inoculation.

C Stage: 14-Liter Fermenter—One liter of B Stage was used to inoculate a 14-liter fermenter containing 9 liters of seed medium:

Seed Medium* - 14-Liter Fermenter

| | |
|---|---|
| Heart Infusion Broth (Difco) | 250 gm |
| NaCl | 50 gm |
| Yeast Extract Dialysate (Amber) | 30 gm |
| (pore size 12,000 mol. wt). | |
| $K_2HPO_4$ | 25 gm |
| UCON LB 625 (8% solution) | 20 ml |
| (presterilized 1 hr. at 121° C.) | |
| Distilled $H_2O$ | 8.5 L |
| Dextrose | 50 gm |
| (sol'n of 50 gm dextrose plus 200 ml distilled $H_2O$ sterilized at 121° C. for 20 min., added aseptically prior to inoculation) | |
| NAD | 100 mg |
| Hemin | 100 mg |

*Sterilized for 90 min. at 121° C.

The fermentation was monitored by optical density (O.D.) and pH determinations until an O.D. of 0.96 was reached.

PRODUCTION—250-LITER FERMENTER

Approximately 10 liters of C Stage was used to inoculate a 250-liter fermenter containing 182 liters of production medium:

PRODUCTION MEDIUM* 250-Liter Fermenter

| | |
|---|---|
| Heart Infusion Broth (Difco) | 5000 gm |
| Yeast Extract Dialysate (Amber) | 600 gm |
| (pore size 12,000 mol. wt). | |
| UCON LB 625 (8% solution) | 400 ml |
| (presterilized 1 hr. at 121° C.) | |
| Dextrose | 1000 gm |
| (sol'n of 100 gm dextrose plus 4 liters distilled $H_2O$ sterilized at 121° C. for 20 min. added aseptically prior to inoculation) | |
| $K_2HPO_4$ | 500 gm |
| NaCl | 1000 gm |
| (salts were dissolved in 4 liters distilled $H_2O$ and sterilized at 121° C. for 20 min. and then added aseptically prior to inoculation) | |
| Hemin 3X | 2 gm |
| (sol'n made by dissolving 2 gm in 50 ml of 0.1M NaOH and adjusting the volume to 1000 ml., sterilized for 20 minutes at 121° C., added prior to inoculaton) | |
| NAD | 100 mg |
| (stock solution of NAD containing 2 mg/ml, sterilized by filtration through a Millipore filter (0.22μ), added prior to inoculation) | |

*Sterilized for 30 min. at 121° C.

The O.D. and pH levels were checked every 2 hours throughout the fermentation. When the O.D. was similar for a two-hour period (final O.D. was 2.80 at 10 hrs.), the fermentation was terminated.

HARVEST AND INACTIVATION

Approximatley 190 liters of the batch were inactivated by harvesting into thimerosal to a final concentration of 1:10000 (w/v).

CENTRIFUGATION

After 24 hours inactivation, the batch was centrifuged in a Sharples centrifuge at a flow rate of 400 ml/min. The supernatant obtained after centrifugation (32,000 rpm) was treated with cetavlon (hexadecyltrimethylammonium bromide) to a final concentration of 0.1% (w/v). The cetavlon-treated supernatant was used for product recovery.

CONCENTRATION BY ULTRAFILTRATION

The supernatant fluid was concentrated at 4° C. on an Amicon DC-30 unit with XM-50 (50,000 Daltons cut-off) hollow fiber cartridges (4.5 $m^2$ membrane area; 2.0 l pm air flow and 20 psi; concentration rate approx. 10 l/hr). After approximately 24 hours the original 180 l. of supernatant fluid was reduced in volume to 4.67 l. of retentate. The filtrate was discarded.

10% ETHANOL PRECIPITATION

To the XM-50 retentate (4.67 liters), 579 ml of 100% ethanol was added dropwise with stirring at 4° C. to a final concentration of 10% ethanol by volume. The mixture was allowed to stir 2-3 additional hours and to stand 12-18 hours at 4° C. to ensure complete precipitation. The supernatant fluid was collected by aspiration and finally by centrifugation in the Beckman J-21B at 11,000×G (8,000 rpm in the JA-10 rotor) for 30 minutes at 4° C. The insoluble pellet was discarded.

20% ETHANOL PRECIPITATION

To the 10% ethanol soluble fraction (5.08 l) 635 ml of 100% ethanol was added dropwise with stirring to a final concentration of 20% by volume. The mixture was allowed to stir 2-3 additional hours and to stand 12-18 hours at 4° C. to ensure complete precipitation. The resulting precipitate was collected as described above (yield 32 grams). The supernatant fluid was processed further.

50% ETHANOL PRECIPITATION

To the 20% ethanol soluble fraction (5.58 l.), 3.35 l of 100% ethanol was added dropwise with stirring to a final concentration of 50% by volume. The mixture was allowed to stand 12-18 hours at 4° C. to ensure complete precipitation.

RECOVERY OF FIRST ETHANOL PELLET

The resulting 20% ethanol soluble/50% ethanol insoluble precipitate was collected by centrifugation in the Beckman J-21B at 11,000×G (8,000 rpm in the JA-10 rotor) for 30 min. at 4° C. The 50% ethanol supernatant fluid was discarded, which resulted in a 226 g yield of a viscous precipitate.

CALCIUM CHLORIDE EXTRACTION

Of the above 50% ethanol insoluble material, 50 g wet paste was mixed with 150.0 ml cold glass-distilled $H_2O$. To this, 200.0 ml of cold 2M $CaCl_2.2H_2O$ was added and the mixture (final concentration=1.0M $CaCl_2$) was extracted in an ice:water bath at setting No. 2 in the Omnimixer for 30 min. The extraction step was repeated three more times as described above to process approximately 200 grams of the wet paste.

20% ETHANOL PRECIPITATION

The $CaCl_2$ extract from above (volume=1600 ml) was brought to 20% ethanol by adding 400 ml of 100% ethanol dropwise with stirring at 4° C. After additional stirring for 2-3 hours, the mixture was allowed to stand 12-18 hours at 4° C. to ensure complete precipitation. The mixture was centrifuged in the Beckman J-21B at 11,000×G (8,000 rm in the JA-10 rotor) for 30 minutes at 4° C. The supernatant fluid was decanted through cheese cloth to remove lipid-like floating material. The insoluble pellet was discarded.

75% ETHANOL PRECIPITATION

The 20% ethanol soluble supernatant fluid (volume=1.86 L) was brought to 75% ethanol by adding 5.15 L of 100% ethanol dropwise with stirring over a 2-3 hour period. The mixture was then allowed to stand 12-18 hours at 4° C. to ensure complete precipitation.

RECOVERY OF THE 75% ETHANOL PELLET

The resulting insoluble precipitate was recovered on a Buchner funnel with a medium glass fritted disc (pore size 10-15 microns), washed three times with 100% ethanol (250 ml per wash) and three times with acetone (250 ml per wash). All washes were discarded. The yield was 56.8 grams.

PHENOL EXTRACTION

A portion (18.2 grams) of material from the previous step was resuspended in 1000 ml (18.2 mg/ml) of 0.488M sodium acetate pH 6.9 with the aid of a Dounce homogenizer. The sodium acetate solution was immediately extracted 4 times with 500 ml each of a fresh aqueous phenol solution made as follows: 900 ml of 0.488M sodium acetate pH 6.9 was added to a five pound bottle of phenol (Mallinckrodt crystalline) and mixed until a complete solution was effected. Each phenol extract was centrifuged for 30 min at 11,000×G at 4° C. in the Beckman J-21B to break the emulsion. The aqueous phases were pooled and extracted 3 additional times with phenol solution in a similar manner. The phenol phases were discarded.

DIALYSIS

The pooled aqueous phases were dialyzed at 4° C. for 22 hours with three 14.0 liter changes of glass distilled $H_2O$. The final dialysis ratio was 1:22,000 volumes and all traces of phenol odor were gone from the sample.

75% ETHANOL PRECIPITATION

To the dialysate (volume=740 ml) was added 18.5 ml of 2.0M $CaCl_2$ to a final concentration of 0.05M $CaCl_2$. The solution was then made 75% ethanol with dropwise addition over 2-3 hrs of 2276 ml of 100% ethanol to the rapidly stirring solution. After standing 12-18 hours more at 4° C., the clear supernatant fluid was siphoned off and the precipitate was collected by centrifugation in the Beckman J-21B at 27,000 G (15,000 rpm for JA-20 rotor) at 4° C. for 30 min. The polysaccharide pellet was titurated in a Waring blender with 500 ml of absolute ethanol, collected on a medium sinter glass funnel and washed with 250 ml of absolute ethanol followed by 250 ml of acetone. The sample was then dried over anhydrous $CaCl_2$ in vacuo at 4° C. for 18-24 hours. The yield was 3.6 grams.

ULTRACENTRIFUGATION IN 20% ETHANOL

The material was resuspended in 200 ml of 0.05M $CaCl_2$ and brought to 20% ethanol with dropwise addition of 50 ml 100% ethanol. The mixture was clarified immediately by centrifugation at 100,000×G (40,000 rpm in the 50.2 Ti rotor) for 2 hrs at 4° C. The pellet was discarded and the clear supernatant fluid (volume=228 ml) was made 75% in ethanol by adding 501.6 ml of 100% ethanol. After stirring 2-3 hrs the mixture was left at 4° C. for 12-18 hrs to ensure complete precipitation.

FINAL POLYSACCHARIDE PRODUCT

The polysaccharide was collected by centrifugation, titurated with ethanol and recovered on a sinter glass funnel. The polysaccharide was washed with absolute ethanol and acetone and dried in vacuo over anhydrous $CaCl_2$ at 4° C. The yield was 3.6 grams of H. influenzae type b capsular polysaccharide. The data of Tables 1-1 and 1-2 were obtained.

TABLE 1-1

| HIB POLYSACCHARIDE CHEMICAL ASSAY DATA | |
| --- | --- |
| Assay | Result |
| Moisture (TG) | 6.4% |
| Protein | 0.1% |
| Nucleic Acid | 0.5% |
| Ribose (pentose) | 28.6% |
| Phosphorus | 5.3% |
| $K_D$ | 0.34 (maj.) |
| | 0.63 (min.) |

The following procedures were used in performing then assays.

1. Moisture—Standard thermogravimetry (wt. loss to 100° C.) using a Perkin-Elmer thermobalance TSG-1.

2. Protein—Lowry method; Lowry et al., J. Biol. Chem., 193: 265 (1951).

3. Nucleic Acid—U. V. method; Warburg and Christian, Biochem Z., 310: 384 (1942).

4. Ribose—Bial method; Dische and Schwartz, Mickorochim Acta 2:13 (1937).

5. Phosphorus—Molybdate method; Chen et al., Anal. Chem. 28: 1756 (1956).

6. $K_D$—Determined on Sepharose 4B using refractive index.

TABLE 1-2

| PYROGENIC SUBSTANCES TEST (Hib Polysaccharide) | |
|---|---|
| Concentration (mcg/ml/kg) | Max. Temp. Rise* 0° C. (3 rabbits) |
| 0.1 (polysac.) | 0.2, 0.2, 0.1 |

*1.0 ml dose

The polysaccharide was further identified by Agar Gel Diffusion. Double diffusion on agar (Ouchterlony) was performed using Hyland pattern D plates. Antiserum prepared against the Ross 768 strain of H. influenzae was placed in the center wells while the bulk polysaccharide, at concentrations of 50, 25, 12.5, 6.2 and 3.1 mcg/ml, was placed in the satellite wells. The plate was incubated at 20°–25° C. in a moist chamber for 24 hours. Precipitin bands (at 0.34 (major) and 0.63) were observed between the bulk polysaccharide and the specific antiserum at concentrations of 50, 25 and 12.5 mcg/ml.

EXAMPLE 2

Preparation of N. Meningitions Type B Serotype 2 Outer Membrane Protein

INOCULUM DEVELOPMENT

A Stage: Mueller-Hinton (MH) agar plates (Difco)—One lyophilized vial was thawed and diluted with 1 ml of Gotschilich's yeast dialysate medium.

The tube was a third generation lyophile obtained by serial culturing and lyophilization of an organism (B-11 strain of N. meningitidis) originally obtained from Walter Reed Army Institute of Research.

Gotschlich's yeast dialysate was prepared as follows:

| Fraction A | GM/L |
|---|---|
| L-glutamic acid | 1.6 |
| NaCl | 6.0 |
| $Na_2HPO_4$.anhydrous | 2.5 |
| $NH_4Cl$ | 1.25 |
| KCl | 0.09 |
| L-cysteine HCl | 0.02 |

Fraction B was obtained by dissolving 1280 gm of Difco Yeast Extract in 6.4 liters of distilled $H_2O$. The solution was dialyzed in the Amicon DC-30 hollow fiber dialysis unit with three H10SM cartridges. The dialysate and 384 gm $MgSO_4.7H_2O$ and 3200 gm dextrose were dissolved in the dialysate and the total volume brought up to 16 liters with distilled water. The pH was adjusted to 7.4 with NaOH and sterilized by filtration through Millipore (0.22μ) and added to fermenter containing "Fraction A" as follows:

For the Nephelometer Flasks: add 1 liter of Fraction A and 25 ml of Fraction B, and adjust pH to 7.0–7.2 with 1 or 2N NaOH.

For the 50 Liter Fermenter: add 39 liters of Fraction A and 800 ml of Fraction B, and adjust pH to 7.0–7.2 with 1 or 2N NaOH.

Mueller-Hinton agar plates (Difco) were streaked (40 per vial) on the day prior to the fermentation run. After 16–18 hours incubation at 37° C. in a water saturated 6%–8% $CO_2$ incubator, the growth in the plates was removed and suspended in 20 ml Gotschlich's yeast dialysate medium.

B Stage: Nephelometer Flasks (2×400 ml in one liter flasks)—The 20 ml growth suspension from Stage A was suspended in 800 ml of Gotschlich's yeast dialysate medium in a one liter nephelometer flask. The pH was adjusted to 7.4–7.6 and the OD was adjusted to 0.06–0.08 at 660 nm.

400 Ml of the growth suspension was transferred to another one liter nephelometer flask. The pH was adjusted continuously between 7.0 and 7.6.

The fermentation was terminated when the culture was in log phase between OD 0.25 and 0.3. The two flasks were pooled (800 ml) into one 1250 bottle.

PRODUCTION

Approximately 800 ml of seed culture was used to inoculate a sterile 50-liter fermenter (Bilthoven) containing 39 liters of complete production medium. The batches were incubated at 37° C., 690 rpm with 5 liters/-min. air overlay and constant pH control at 7.0–7.2. The pH and dissolved oxygen concentrations were determined continuously throughout the fermentations. After 17 h the culture was inactivated with phenol (final concentration 0.5% v/v). The final O.D. was 1.60 after 17 hours.

INACTIVATION

A sample was taken 2 hours after inactivation and checked for viability. There was no growth observed on any of the plates after 24–48 hours, indicating that the culture was inactivated.

CENTRIFUGATION

After at least 24 h at 4° C., the 40 liters of inactivated culture fluid was concentrated on a Millipore Pellicon Cassette system (0.45 micron with 10 sq. ft. membrane) to 3 liters. The remaining 3L of cell suspension was centrifuged at 10,000 rpm, 40 min. at 4° C. in a GS3 Sorvall rotor. The cell paste (200 grams wet weight) was then collected.

WASHING AND EXTRACTION

The bacterial cells were resuspended gently (with magnetic stirring) in 800 ml of distilled water (2% of original growth volume) and pelleted by centrifugation at 11,000 G (8000 rpm in FA-10 rotor) for 30 min at 5° C.

The washed bacterial cells were suspended (with very gentle magnetic stirring) at 5 ml/g wet weight in 1000 ml of 0.1M Tris-0.01M EDTA, pH 8.5 buffer containing 0.5% sodium deoxycholate (DOC) and heated to 56° C. in a water-bath. After the temperature of the mixture had reached 56° C., the extraction was continued with gentle shaking for 15 min. The extract was centrifuged at 15,000 G (10,000 rpm) for 1 hour at 4° C. in a Beckman L5-65 centrifuge using Type 19 Ti rotor.

The cloudy supernatant fluids were gently aspirated and re-centrifuged in the same rotor at 31,000 G (14,500 rpm) for 30 min to achieve clarification. The 15,000 G pellets were re-extracted (as described above) in 1000 ml of 0.5% DOC, 1M Tris—0.01M EDTA, pH 8.5 buffer at 56° C. for 15 min. The second extract was centrifuged in the Type 19 Ti rotor for 45 min at 31,000 G (14,500 rpm). The two extraction supernatant fluids were combined and re-centrifuged for 60 min at 31,000 G in the Type 19 Ti rotor.

ULTRACENTRIFUGATION

The pooled supernatant fluid was centrifuged in batches of 400 ml each at 100,000 G (40,000 rpm in 45 Ti rotor) for 2 hours. The 100,000 G pellets which contain the serotype 2 protein, were washed twice by suspending (using a Dounce homogenizer) in 400 ml of the above 0.5% DOC buffer, heating at 56° C., for 15 min and re-centrifuging at 100,000 G for 2 hours as described above.

FINAL PROTEIN PRODUCT

The 100,000 G pellets from above were resuspended in 105 ml of pyrogen-free distilled water with the aid of a Dounce homogenizer. The suspension was centrifuged at 12,000 G (10,000 rpm) for 15 min in a Beckman J-21C centrifuge at 4° C. using a JA-20 rotor. The pellet (which contained highly aggregated serotype protein) was discarded and the supernatant fluid (102 ml), which contained the serotype 2 protein, was made 1/20,000 in thimerosal (sodium ethylmercurithiosalicylate) and stored at 4° C. The data of Tables 2-1 and 2-2 were obtained.

TABLE 2-1

MENINGOCOCCAL B SEROGROUP 2 PROTEIN SOLUTION CHEMICAL ASSAY DATA

| Assay | Result |
|---|---|
| Protein | |
| Lowry | 5.4 mg/ml |
| UV | 3.8 mg/ml |
| Adsorb. 280 nm/260 nm. | 1.01 |
| Nucleic Acid* | |
| UV | 2.0% (wt./wt.) |
| Bial | 2.1% (wt./wt.) |
| Diphenylamine | 0.1% (wt./wt.) |
| Neutral Sugars* | 0.9% (wt./wt.) |
| Sialic Acid* | 2.4% (wt./wt.) |
| Molecular Weight | |
| SDS-PAGE | 41,000 d |

*Calculated as percent of Lowry protein in solution.

In addition to the test methods described in Table 1-1, the following procedures were used.

1. Nucleic Acid—Color development was observed with the orcinol reaction (Bial) which corresponded to 2.1% RNA calculated as a percentage of the protein concentration. The diphenylamine test for DNA indicated a 0.1% DNA content calculated as a percentage of the protein in the bulk solution.
2. Neutral Sugars—The neutral sugar content calculated as a percentage of protein was found using the anthrone colorimetric test. (Scott and Melvin, Anal. Chem. 25, 1656 (1953).
3. Sialic Acid—The sialic acid content was found using the resorcinol-HCl method (Svennerholm, Biochem. Biophys., Acta 24, 604 (1957).
4. Molecular Weight—The molecular weight of the mercaptoethanol denatured protein as determined by SDS polyacrylamide gel electrophoresis (Nature 227: 680 (1970), LKB Application Note 306).

TABLE 2-2

PYROGENIC SUBSTANCES TEST
N. MENINGITIDIS GROUP B SEROTYPE 2 PROTEIN

| Concentration (mcg/ml/kg) | Max. Temp. Rise* 0° C. (3 rabbits) |
|---|---|
| 0.025 (protein) | 0.2, 0.0, 0.1 |

*1.0 ml dose

The protein was further identified by a ring test (Experimental Immuno-Chemistry, (1967), C. C. Thomas, Springfield, Ill.) performed using the bulk protein (525 γ/ml) and antiserum prepared against both whole organism meningococcal group B and a meningococcal group B protein. A large precipitate was visible in both antiserum preparations after overnight incubation at room temperature.

EXAMPLE 3

Preparation of H. Influenzae Type B Conjugate Vaccine

PREPARATION OF H. INFLUENZAE B POLYSACCHARIDE-6-AMINOCAPROIC ACID COMPLEX 1. 250 Mg of the polysaccharide of Example 1 was dissolved in 50 ml of distilled water and cooled to 4° on ice. The polysaccharide solution was kept on ice throughout the reaction.
2. Cyanogen bromide (CNBr, Eastmen Kodak Co.) was prepared in distilled water at 100 mg/ml.
3. 1.25 Gm of 6-aminocaproic acid was dissolved in 12.5 ml of 0.5M borate buffer pH 8.5 in a 125 ml Vitro bottle with screw cap. The borate buffer was prepared as follows: 30.9 g of boric acid (Sigma) in distilled water and tritrate with 1N NaOH to give a final volume of 1000 ml.
4. 6-Aminocaproic acid solution was also kept on ice throughout the activation reaction.
5. pH Of the polysaccharide solution was adjusted to 10.5 with 0.10N NaOH using pH meter 26 (Radiometer) which was calibrated to 4°.
6. 75 Mg of CNBr (750 μl) was then added to the polysaccharide solution and the pH of the solution was maintained at pH 10.5 immediately with 0.10N NaOH and adequate stirring.
7. The activation proceeded for 6 minutes. At the end of activation, the polysaccharide solution was transferred to the 6-aminocaproic acid solution with hand mixing.
8. The mixture was incubated at 4° with gentle stirring for 20–24 hours. The tube was wrapped with aluminum foil to avoid light.
9. The complex was dialyzed against 20 liter of distilled water in Spectrapor membrane tubing, 45 mm, m. wt. cutoff 12,000–14,000, overnight (20–24 hours) at 4° with one change of distilled water.
10. The polysaccharide-spacer complex was then lyophilized and stored at 4°.

PREPARATION OF SEROTYPE PROTEIN FOR POLYSACCHARIDE COUPLING

The serotype protein of Example 2 was prepared in $H_2O$ at a concentration of 5.7 mg/ml. The protein was diluted with distilled water to 5 mg/ml before use.

PREPARATION OF CONJUGATE

1. The lyophilized polysaccharide-spacer complex was dissolved in 40 ml (200 mg) of the protein solution.
2. The pH of the mixture adjusted between 5.1–5.0 with 0.01N HCl.
3. 1-Ethyl-3-(3-dimethylaminopropyl)-Carbodiimide Hydrochloride (EDC, Sigma) was prepared at 100 mg/ml in distilled water.
4. 200 Mg (2.00 ml) of EDC was added to the polysaccharide-protein solution.
5. The pH of the solution was titrated constantly to 4.75 using an ETS 822 end point titration system in the pH stat mode (Radiometer, Ranin Instrument Co., Inc.). The titration is initiated upon the addition of EDC.
6. The reaction proceeded for 120 minutes at pH 4.75.

7. At the end of this time, the pH of the solution was brought to 7.0 with 0.25N NaOH to stop the reaction.

PURIFICATION OF CONJUGATE

1. The conjugate from the coupling reaction was centrifuged at 12,000×g (10,000 rpm) in a Sorvall SS-34 rotor for 5 minutes in a Sorvall RC2B centrifuge at 4°.
2. The supernate was removed carefully and placed on a Sepharose CL-4B column (5×100 cm) equilibrated and eluted with 0.2M ammonium acetate buffer (made by dilution from 10X stock solution of 2M ammonium acetate 154.2 g/L distilled water, Sigma Chemical Co., with 1% thimerosal, 1:200). The column was run at a flow rate of 40 ml/hour at room temperature. Fractions were collected with an LKB 7000 Ultrorac equipped with an LKB Unicord II and an LKB 6520-3 recorder. Fractions were monitored at a wavelength of 260 nm to follow the protein in the conjugate.
3. At the end of column, 100 μl aliquots were taken from every other fraction and assayed for polysaccharide by Bial reaction. Two peaks were obtained based on the Bial reaction. The first peak at the void volume contained the conjugate and the second peak contained the unreacted free polysaccharide.
4. The fractions that contained the conjugate were pooled and the pooled conjugates were assayed for polysaccharide and protein content.
5. Two conjugation runs at 250 mg of polysaccharide and 200 mg of protein were carried out. Conjugates 1 and 2 were dialyzed separately against 18 L of physiological saline in the presence of 1:20,000 thimerosal for 24 hours with one change of 18L of physiological saline. The results are summarized below.

| Con-jugate | Protein | Polysac. (PS) | Total Vol. | PS/Prot. | Yield of PS |
|---|---|---|---|---|---|
| 1. | 1010 μg/ml | 195 μg/ml | 163 ml | 0.19 | 13% |
| 2. | 840 μg/ml | 164 μg/ml | 200 ml | 0.18 | 13% |

6. Conjugates 1 and 2 were pooled and dialyzed vs. physiological saline in the presence of 1:20,000 thimerosal. The final chemical analysis of the pooled conjugate is shown below:

| Protein | Polysac. (PS) | Total Vol. | PS/Prot. | Total Prot. | Total PS |
|---|---|---|---|---|---|
| 950 μg/ml | 175 μg/ml | 367 ml | 0.18 | 349 mg | 64 mg |

FINAL CONJUGATE PRODUCT

The pooled conjugate vaccine was diluted 1:3 in physiological saline (365 ml conjugate in 730 ml saline) containing 0.005% thimerosal and gently agitated on a rotary shaker for 20 minutes. Sterile vials were prepared and stored at 4° C. The data of Table 3-1 and 3-2 were obtained.

TABLE 3-1

Polysaccharide-Protein Conjugate Chemical Assay Data

| Assay | Result |
|---|---|
| Ribose (Bial) | 14.4 mcg/ml (corresponds to 50.3 mcg/ml of PS) |
| Protein (Lowry) | 265 mcg/ml |
| pH | 7.6 |
| Nephelos | 520 scatter units |

1. Nephelos—The nephelos of the final vaccine container was determined by using a Beckman ICS Analyzer II in the scatter mode (M11 gain). The instrument was standardized with Beckman's scatter reference solution No. 5930.

TABLE 3-2

Polysaccharide-Protein Conjugate Pyrogenic Substances Test

| Conc. (mcg/ml/kg) | Max. Temp. Rise* 0° C. (3 rabbits) |
|---|---|
| 0.025 (conjugate) | 0.3, 0.0, 0.5 |

*1 ml dose

The degree of immune response and the class of antibody elicited vary with the protein carrier. As a demonstration of this, a conjugate vaccine (prepared substantially as in Example 3 except that the *N. meningitidis* type B protein used is a surface protein other than the serotype outer membrane protein of Example 2) has been compared to a vaccine prepared as in Example 3. The conjugate vaccine from serotype outer membrane protein exhibits a significantly superior response. Specifically, the serotype outer membrane protein conjugate produces primarily $I_gG$ antibodies, whereas the other conjugate produces primarily $I_gM$ antibodies.

EXAMPLE 4

Preparation of *H. Influenzae* Type B Conjugate Vaccine (Non-Serotype Protein)

PREPARATION OF H. INFLUENZAE B POLYSACCHARIDE-6-AMINOCAPROIC ACID COMPLEX

Following substantially the same procedure as in Example 3 on a different lot of Hib PS, a polysaccharide-spacer complex was prepared, lyophilized, and stored at 4° C.

PREPARATION OF PROTEIN FOR POLYSACCHARIDE COUPLING

250 Mg (50 ml) of purified non-serotype protein was dialyzed against 20L of distilled water for 20 hours at 4° C. using Spectrapor membrane tubing, 45 mm m. wt. cutoff 12,000–14,000, with one change of distilled water. The pH of the distilled water was adjusted to 7.4 with 1N NaOH before use.

PREPARATION OF CONJUGATE

1. The lyophilized polysaccharide-spacer complex was dissolved in 50 ml of the protein solution.
2. The pH of the mixture adjusted between 5.1–5.0 with 0.01N HCl.
3. 1-Ethyl-3-(3-dimethylaminopropyl)-Carbodiimide Hydrochloride (EDC, Sigma) was prepared at 250 mg/ml in distilled water.
4. 750 Mg (3.00 ml) of EDC was added to the polysaccharide-protein solution in three aliquots 10 minutes apart.
5. The pH of the solution was titrated constantly to 4.75 using an ETS 822 end point titration system in the pH stat mode (Radiometer, Ranin Instrument Co., Inc.), initiated upon the addition of EDC.

6. The reaction was proceeded for 20-25 minutes at pH 4.75.

7. At the end of this time, the pH of the solution was brought to 7.0 with 0.25N NaOH to stop the reaction.

PURIFICATION OF CONJUGATE

1. The conjugate from the coupling reaction was centrifuged at 12,000×g (10,000 rpm) in a Sorvall SS-34 rotor for 5 minutes in a Sorvall RC2B centrifuge at 4° C.

2. The supernate was removed carefully and placed on a Sepharose CL-4B column (5×100 cm) equilibrated and eluted with 0.2M ammonium acetate buffer (made by dilution from 10X stock solution of 2M ammonium acetate 154.2 g/L distilled water, Sigma Chemical Co., with 1% thimerosal, 1:200). The column was run at a flow rate of 40 ml/hour at room temperature. Fractions were collected with an LKB 7000 Ultrorac equipped with an LKB Unicord II and an LKB 6520-3 recorder. Fractions were monitored to follow the protein in the conjugate.

3. At the end of column, 100 μl aliquots were taken from every other fraction and assayed for polysaccharide by Bial reaction. Two peaks were obtained based on the Bial reaction. The first peak at the void volume contained the conjugate and the second peak contained the unreacted free polysaccharide.

4. The fractions that contained the conjugate were pooled and the pooled conjugates were assayed for polysaccharide and protein content.

5. Two conjugate lots were prepared according to the procedure described above, combined, and dialyzed against 15L of 0.85% saline in the presence of 1:20,000 thimerosal for 36 hours with two changes of 0.85% saline. The conjugate was stored at 4° until use. The final chemical analysis of the pooled conjugate is shown below:

| Protein | Polysac. (PS) | Total Vol. | PS/Prot. | Total Prot. | Total PS |
|---|---|---|---|---|---|
| 940 μg/ml | 166 μg/ml | 295 ml | 0.18 | 277 mg | 49 mg |

The data of Table 4-1 were obtained.

TABLE 4-1

PYROGENIC SUBSTANCES TEST
Hib PS-NON-SEROTYPE PROTEIN CONJUGATE

| Conc. (mcg/ml/kg) | Max. Temp. Rise* 0° C. (3 rabbits) |
|---|---|
| 0.25 (conjugate) | 0.0, 0.0, 0.1 |

*1.0 ml dose

FINAL CONJUGATE PRODUCT

The pooled conjugate vaccine was diluted 1:3 in physiological saline (290 ml conjugate in 580 ml saline) containing 0.005% thimerosal and gently agitated on a magnetic base for 10 minutes. Sterile vials were filled and stored at 4° C. The data of Table 4-2 were obtained.

TABLE 4-2

Polysaccharide-Non-serotype Protein Conjugate Chemical Assay Data

| Assay | Result |
|---|---|
| Ribose (Bial) | 15.7 mcg/ml (corresponds to 55.3 mcg/ml of polysaccharide) |
| Protein (Lowry) | 313 mcg/ml |
| pH | 7.8 |
| Nephelos | 568 scatter units |

EXAMPLE 5

IMMUNOGLOBUBULIN CLASS RESPONSE TO HIB PS/PROTEIN CONJUGATES

Hib PS/protein conjugates were used to induce antibody responses in mice. Surprisingly, it was found that the conjugate prepared from serotype outer membrane protein, prepared substantially as in Example 3, produced a different class of antibodies when compared to conjugate from non-serotype proteins, prepared as in Example 4. Specifically, the conjugate of this invention produces primarily IgG whereas conjugate from Example 4 produces primarily IgM. The data of Table 5-1 were obtained.

TABLE 5-1

IMMUNOGLOBULIN CLASS RESPONSE TO INFLUENZAE TYPE B CONJUGATES

| Conjugate | Dose* (mcg/0.5 ml) | | Bleeding day | Immunoglobulin | |
|---|---|---|---|---|---|
| | | | | Ig M (%) | Ig G (%) |
| Non-serotype Protein | 10.0 | (2 doses) | 21 | ≧3450 (≧86) | 550 (≧14) |
| | | (2 doses) | 52 | 2535 (94) | 165 (6) |
| Serotype Outer Mem. Protein | 10.0 | (1 dose) | 21 | 2150 (60) | 1450 (40) |
| | | (1 dose) | 52 | 1750 (53) | 1550 (47) |
| | | (2 doses) | 21 | 0 (0) | ≧4000 (100) |
| | | (2 doses) | 52 | 0 (0) | ≧4000 (100) |

*Mice injected subcutaneously on day 0 and bled day 21 (1 dose) or injected days 0 and 14 with a day 21 bleeding.
**2 Mercaptoethanol treatment of mouse serum pools. Sera assayed by RIA.

What is claimed is:

1. A polysaccharide/protein conjugate which comprises H. influenzae type B polysaccharide and a T-cell stimulating N. meningitidis serotype outer membrane protein, said polysaccharide and protein being coupled through 6-aminocaproic acid.

2. A conjugate of claim 1 wherein the protein is N. meningitidis type B, serotype outer membrane protein.

3. A composition comprising an effective amount for either active or passive immunization of mammalian species, of the polysaccharide/protein conjugate which comprises H. influenzae type b polysaccharide and a T-cell-stimulating N. meningitidis serotype outer membrane protein, said polysaccharide and protein being coupled through 6-aminocaproic acid, antisera derived from said conjugate, or gammaglobulin or other antibody-containing fractions of said antisera, and a pharmaceutically-acceptable carrier.

4. A composition according to claim 3, further comprising an adjuvant.

5. A composition according to claim 3, wherein an effective amount is 2–50 μg of the conjugate.

6. A method of treating mammalian species which comprises administering to said species an immunologically effective amount of a composition comprising a polysaccharide/protein conjugate which comprises *H. influenza* type b polysaccharide and a T-cell-stimulating *N. meningitidis* serotype outer membrane protein, said polysaccharide and protein being coupled through 6-aminocaproic acid, and a member of the group consisting of a pharmaceutically-acceptable carrier, an adjuvant, and a pharmaceutically-acceptable carrier and adjuvant.

7. The method according to claim 6 wherein the species to be treated is human neonates, and the effective amount of the composition per dose is an amount corresponding to 10 μg of the conjugate.

* * * * *